US010632055B2

(12) United States Patent
Goutsis et al.

(10) Patent No.: US 10,632,055 B2
(45) Date of Patent: Apr. 28, 2020

(54) METHOD AND KIT FOR COLORING OF HAIR WITH ACID DYES

(71) Applicant: Henkel AG & Co. KGaA, Duesseldorf (DE)

(72) Inventors: Konstantin Goutsis, Juechen (DE); Daniela Kessler-Becker, Leverkusen (DE); Jing Hodes, Hagen (CN)

(73) Assignee: Henkel AG & Co. KGaA, Duesseldorf (DE)

(*) Notice: Subject to any disclaimer, the term of this patent is extended or adjusted under 35 U.S.C. 154(b) by 0 days.

(21) Appl. No.: 15/936,637

(22) Filed: Mar. 27, 2018

(65) Prior Publication Data
US 2018/0289604 A1 Oct. 11, 2018

(30) Foreign Application Priority Data

Apr. 10, 2017 (DE) .................. 10 2017 206 087

(51) Int. Cl.
A61Q 5/10 (2006.01)
A61K 8/365 (2006.01)
A61K 8/44 (2006.01)
A61K 8/46 (2006.01)
A61K 8/81 (2006.01)

(52) U.S. Cl.
CPC .............. A61K 8/365 (2013.01); A61K 8/442 (2013.01); A61K 8/466 (2013.01); A61K 8/8182 (2013.01); A61Q 5/10 (2013.01); A61K 2800/4324 (2013.01); A61K 2800/884 (2013.01)

(58) Field of Classification Search
CPC ........ A61Q 5/10; A61K 8/22; A61K 2800/88; A61K 2800/884; A61K 8/046; A61K 8/365; A61K 8/36; A61K 8/361; A61K 2800/432; A61K 2800/4324
See application file for complete search history.

(56) References Cited

U.S. PATENT DOCUMENTS

| 2006/0248661 | A1* | 11/2006 | Wood ............... A61K 8/411 8/405 |
| 2007/0033744 | A1* | 2/2007 | Kravtchenko ....... A61K 8/23 8/405 |
| 2017/0100322 | A1 | 4/2017 | Kerl et al. |
| 2017/0189310 | A1 | 7/2017 | Lago et al. |

FOREIGN PATENT DOCUMENTS

| EP | 0815828 | A1 | | 1/1998 | |
| EP | 1237660 | B1 | | 8/2006 | |
| GB | 2552862 | A | | 2/2018 | |
| JP | 2004189745 | A | * | 7/2004 | ............... A61Q 5/10 |
| WO | 2007083206 | A1 | | 7/2007 | |
| WO | 2007086730 | A2 | | 8/2007 | |
| WO | 2007091882 | A1 | | 8/2007 | |
| WO | 2015090804 | A1 | | 6/2015 | |

OTHER PUBLICATIONS

English translation of the Patent JP 2004189745 A. (Jul. 2004).*
Intellectual Property Office, Search Report under Section 17(5) for United Kingdom Patent Application No. GB1805905.5 dated Oct. 30, 2018.

* cited by examiner

Primary Examiner — Eisa B Elhilo
(74) Attorney, Agent, or Firm — Lorenz & Kopf, LLP

(57) ABSTRACT

The subject of the present disclosure is a method for coloring of keratinous fibers, particularly human hair, including the following steps in the specified sequence:
A) Treatment of the fibers with a hydrous pre-treatment agent (V),
B) Treatment of the fibers with a hydrous coloring agent (F), wherein
the pre-treatment agent (V) has a pH value of from about 1.0 to about 5.0 and
the coloring agent (F) has at least one partially-oxidizing acid dye and a pH value of from about 5.0 to about 9.5. An additional subject of the present disclosure is a multi-component package unit (kit) including a pre-treatment agent (V) and a coloring agent (F).

20 Claims, No Drawings

METHOD AND KIT FOR COLORING OF HAIR WITH ACID DYES

CROSS-REFERENCE TO RELATED APPLICATION

This application claims priority to German Patent Application DE102017206087.5, filed Apr. 10, 2017, which is incorporated herein by reference in its entirety.

TECHNICAL FIELD

The subject of the present application is a method for dyeing keratinous fibers, particularly human hair, which comprises the pre-treatment of the hair with a pre-treatment agent and a subsequent coloring step. The pretreatment agent is acidified, whereas the colorant contains at least one acid dye and has a neutral to basic pH. Use of the new method enables a reduction of skin coloring during dyeing with acid dyes.

BACKGROUND

A second subject of the present disclosure is a multi-component package unit (kit-of-parts, or also kit) containing two separate agents packaged separately in at least two containers, which are applied in the aforementioned method. The kit-of-parts comprises a first container which contains a hydrous acidified pre-treatment agent. The coloring agent, which contains at least one acid dye and one neutral to basic pH value is contained in a second container.

Changing the form and color of keratinous fibers, more particularly of hair, constitutes an important area of modern cosmetics. Consequently, the hair's appearance can be adapted both to current fashion trends and also to the particular preferences of each and every person. In order to change the hair color, the person skilled in the art knows various staining systems depending on requirements for the coloration. Oxidation coloring dyes are usually used for permanent, intense coloring with good fastness properties and good coverage of gray. Such colorants usually contain oxidation dye precursors, so-called developer components and coupler components, which form the dyes under the influence of oxidants, such as hydrogen peroxide. Oxidation dyes are exemplified by outstanding, long-lasting coloring results, but are also associated with a certain amount of hair damage. With an emphasis particularly on low-damage coloring, therefore, use of oxidation dyes is not the first method of choice.

The color of hair can be changed temporarily by employing partially-oxidizing dyes. In this process, dyes already formed diffuse from the colorant into the hair fibers. In comparison oxidative hair coloring, the colors obtained with partially-oxidizing dyes has lower stability and washes out more quickly.

The gray coverage that can be achieved with partially-oxidizing dyes is generally in need of improvement. However, the low hair damage of dyeing with partially-oxidizing dyes is advantageous.

There are various substance classes available to the person skilled in the art for coloring with partially-oxidizing dyes, such as nitro dyes, anthraquinone dyes, azo dyes or triarylmethane dyes. Furthermore, it is also possible to classify dyes in different categories depending on their charge. Dyes with a cationic charge are usually referred to as "basic dyes"; a person skilled in the art knows dyes with an anionic charge by the term "acid dyes".

Acid dyes within the group of partially-oxidizing dyes have the best fastness properties. However, the coloring effect of acid dyes depends heavily on the pH value. In order to achieve an intense color result, the agents applied on the keratinous fibers must usually have a pH value of less than about 5. A pH value of less than about 3 is particularly preferred.

A disadvantage of acid dies is their often very pronounced skin coloring. In this case, the coloring of the hair and the skin coloring occur in parallel. The more intense the hair color, the stronger the skin coloring usually is on all body parts that come into contact with the coloring agent during the dyeing process.

Therefore, the present disclosure addresses the problem of reducing skin coloring during dyeing with acid dyes.

BRIEF SUMMARY

Method and multi-component package units for coloring of keratinous fibers are provided herein. In an exemplary embodiment, a method for coloring of keratinous fibers includes treating the fibers with a hydrous pre-treatment agent (V). The fibers are further treated with a hydrous coloring agent (F). The hydrous pre-treatment agent (V) has a pH value of from about 0 to about 4.5, and the hydrous coloring agent (F) has at least one partially-oxidizing acid dye and a pH value of from about 5.0 to about 9.5.

In another exemplary embodiment, a multi-component package unit (kit-of-parts) for coloring of keratinous fibers includes, separately packaged, a first container (I) including a hydrous pre-treatment agent (V). A second container (II) includes a hydrous coloring agent (F). The hydrous pre-treatment agent (V) has a pH value of from about 0 to about 4.5, and the hydrous coloring agent (F) has at least one partially-oxidizing acid dye and a pH value of from about 5.0 to about 9.5.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Surprisingly, it has been found that the aforementioned problem can be solved when a sequential method is used for dying the hair, wherein the hair is treated with a pre-treatment agent before use of the acid dyes. The pre-treatment agent has an acidic pH value and, therefore, the pH value in the keratinous fibers is also reduced, whereby the optimal pH range for the coloring is generated. After the pre-treatment, the actual coloring agent with the acid dyes is applied, wherein the coloring agent itself is not acidic and has a neutral to basic pH value. Intense coloring is not achieved with use of the coloring agent alone. Therefore, significant coloring only occurs in areas that are treated with the pre-treatment agent and the coloring agent. By using this method, hair could be dyed with an intense coloring result while minimizing the skin coloring of the adjoining skin areas.

A first subject of the present disclosure is a method for coloring of keratinous fibers, particularly human hair, including the following steps in the specified sequence:
A) Treatment of the fibers with a hydrous pre-treatment agent (V),
B) Treatment of the fibers with a hydrous coloring agent (F), wherein
the pre-treatment agent (V) has a pH value of from about 0 to about 4.5 and
the coloring agent (F) has at least one partially-oxidizing acid dye and a pH value of from about 5.0 to about 9.5.

Keratinous fibers, keratin-containing fibers or keratin fibers are furs, wool, feathers and, in particular, human hair. Although the agents as contemplated herein are most suitable for lightening and coloring keratin fibers, they can in principle be used for other purposes.

The successive use of pre-treatment agent (V) and coloring agent (F) characterize the inventive method. These two agents are different cosmetic agents which contain all essential ingredients in a cosmetic container. An essential characteristic feature of both agents is their respective pH value. The pre-treatment agent (V) and the coloring agent (F), therefore, are both hydrous. The cosmetic carrier can be a suitable hydrous, alcoholic or hydrous-alcoholic carrier. For example, the pre-treatment agent (V) and the coloring agent (F) can each have the form of an emulsion, a gel or in the form of a foaming solution containing surfactants, a foam aerosol, a foam formulation or in the form of another preparation which is applied to the keratinous fibers which is suitable for use on the hair. It is particularly preferred that the pre-treatment agent (V) is used in the form of a foam.

Use of the pre-treatment agent (V) in the inventive process takes place first in step A), followed by application of the coloring agent (F) in step B).

The pre-treatment (V) is applied in order to adjust an acidic pH value appropriate to the keratinous fibers, which enables intense coloring of the hair fibers in the subsequent application of the coloring agent (F). For this reason, the sequence of steps A) and B) as contemplated herein takes place within an application process, wherein a maximum period of about 24 hours, preferably about 12 hours, more preferably about 6 hours and particularly about 3 hours elapses between the sequence of steps A) and B).

In a possible embodiment, the pre-treatment agent (V) is applied to the keratinous fibers in step A) and rinsed out after a dwell time that can last from about 30 seconds to about 45 minutes. Then, after the pre-treatment agent (V) is rinsed out, the coloring agent (F) is applied in the subsequent step B), allowed to take effect for a period of from about 30 seconds to about 45 minutes and then also rinsed out.

Therefore, a method as contemplated herein comprising the following steps in the specified sequence is suitable
A1) Application of a pre-treatment agent (V) on the fibers,
A2) Allowing the pre-treatment agent (V) to take effect for a period of from about 30 seconds to about 45 minutes,
A3) Rinsing out of the pre-treatment agent (V),
B1) Application of a coloring agent (F) on the fibers,
B2) Allowing the coloring agent (F) to take effect for a period of from about 30 seconds to about 45 minutes
B3) Rinsing out of the coloring agent (F),
wherein
the pre-treatment agent (V) has a pH value of from about 0 to about 4.5 and
the coloring agent (F) has at least one partially-oxidizing acid dye and a pH value of from about 5.0 to about 9.5.

A method as contemplated herein comprising the following steps in the specified sequence is also suitable
A1) Application of a pre-treatment agent (V) on the fibers,
A2) Allowing the pre-treatment agent (V) to take effect for a period of from about 30 seconds to about 45 minutes,
A3) Rinsing out of the pre-treatment agent (V),
B1) Application of a coloring agent (F) on the fibers,
B2) Allowing the coloring agent (F) to take effect for a period of from about 30 seconds to about 45 minutes
B3) Rinsing out of the coloring agent (F),
wherein
the pre-treatment agent (V) has a pH value of from about 0 to about 4.5 and
the coloring agent (F) has at least one partially-oxidizing acid dye and a pH value of from about 5.0 to about 9.5 and
wherein
a period of from about 10 seconds to about 48 hours elapses between steps A3 and B1), preferably from about 10 seconds to about 24 hours, more preferably from about 10 seconds to about 12 hours and particularly from about 10 seconds to about 30 minutes.

The minimum time period of about 10 seconds is the minimum duration after the washing out of the previously applied agent is finished which the user usually needs to grasp the next agent, the container in which it was prepared, remove it and apply it on the keratinous fibers.

The washing out of the pre-treatment agent (V) in step A3) and/or the washing out of the coloring agent (F) in step B3) can be carried out with water or water with the aid of a shampoo, a conditioning shampoo or a conditioner. Moreover, it is also possible to rinse out the pre-treatment agent (V) in step A3) with water and to rinse out the coloring agent (F) in step B3) with water or with the aid of a shampoo, a conditioning shampoo or a conditioner.

However, in the context of work resulting in this present disclosure, it has been found that particular preference is given to developing the pre-treatment agent (V) as a "leave-on" product. Within this particularly preferred embodiment, the pre-treatment agent (V) is applied to the keratinous fibers in step A) and allowed to take effect for a period of from about 30 seconds to about 45 minutes. Then, the subsequent application of coloring agent (F) in step B) takes place without intermediate rinsing out of the pre-treatment agent (V), i.e. in step B) the coloring agent (F) is applied to the keratinous fibers with the agent (V) still in place. Now the agents (V) and (F), which are on the keratinous fibers together, are allowed to take effect for a period of from about 30 seconds to about 45 minutes and then rinsed out. The collective rinsing out of pre-treatment agent (V) and coloring agent (F) can take place with water or water with the aid of a shampoo, a conditioning shampoo or a conditioner.

Therefore, particular preference is given to a method as contemplated herein comprising the following steps in the specified sequence
A1) Application of a pre-treatment agent (V) on the fibers,
A2) Allowing the pre-treatment agent (V) to take effect for a period of from about 30 seconds to about 45 minutes,
B1) Application of a coloring agent (F) on the fibers on which the pre-treatment agent (V) is still in place,
B2) Allowing the both agents (V) and (F) to take effect for a period of from about 30 seconds to about 45 minutes,
B3) Rinsing out of both agents (V) and (F),
wherein
the pre-treatment agent (V) has a pH value of from about 0 to about 4.5 and
the coloring agent (F) has at least one partially-oxidizing acid dye and a pH value of from about 5.0 to about 9.5.

Kit-of-Parts

To apply the method as contemplated herein, it is particularly comfortable for the user when they use the agents that are prepared for them in the form of a multi-component package unit successively (i.e. in the form of a kit-of-parts, or kit).

A second subject of the present disclosure, therefore, is a multi-component package unit (kit-of-parts) for dyeing of keratinous fibers, particularly human hair, which are packaged separately from each other, comprising
(I) a first container (I) containing a hydrous pre-treatment agent (V) and (II) a second container (II) containing a hydrous coloring agent (F),
wherein
the pre-treatment agent (V) has a pH value of from about 0 to about 4.5 and
the coloring agent (F) has at least one partially-oxidizing acid dye and a pH value of from about 5.0 to about 9.5.

Also applicable for the kit: It is characteristic for the multi-component package unit as contemplated herein that it comprises at least two containers, wherein the first container contains a pre-treatment agent (V) and the second container contains a coloring agent (F). These two agents are different cosmetic agents which contain all essential ingredients in a cosmetic container. An essential characteristic feature of both agents is their respective pH value. The pre-treatment agent (V) and the coloring agent (F), therefore, are both hydrous. Therefore, the cosmetic carrier is preferably a suitable hydrous, alcoholic or hydrous-alcoholic carrier. For example, the pre-treatment agent (V) and the coloring agent (F) can each have the form of an emulsion, a gel or in the form of a foaming solution containing surfactants, a foam aerosol, a foam formulation or in the form of another preparation which is applied to the keratinous fibers which is suitable for use on the hair.

In addition to the first and second container, the kit-of-parts as contemplated herein also comprises an additional container with additional agents. For example, a third separately packaged container can also be optionally included, which contains, for example, a conditioner or a shampoo.

However, it is preferable that the inventive multi-component package unit comprises exactly two containers. Should an additional nurturing and/or cleaning effect be produced in the context of this particularly preferred embodiment, the nurturing, conditioning and/or cleaning ingredients that can be optionally used for this purpose are added to either the pre-treatment agent (V), the coloring agent (F) or both agents (V) and (F).

Therefore, preference is given to a multi-component package unit (kit-of-parts) for dyeing of keratinous fibers, particularly human hair, comprising exactly two containers packaged separately from each other, wherein
(I) the first container (I) containing a hydrous pre-treatment agent (V) and
(II) the second container (II) contains a hydrous coloring agent (F), and
the pre-treatment agent (V) has a pH value of from about 0 to about 4.5 and
the coloring agent (F) has at least one partially-oxidizing acid dye and a pH value of from about 5.0 to about 9.5.
Container (I)

In the context of the method as contemplated herein, the pre-treatment agent (V) is applied to the fibers first. For this purpose, the multi-components package unit as contemplated herein comprises a first container (I), containing the pre-treatment agent (V).

With use of the pre-treatment agent, the pH value on or in the hair should be purposefully adjusted to a low range. In order to effectively reduce skin coloring, it is particularly preferred that the pre-treatment agent (V) is only applied on the hair and contact with all skin areas adjoining all of the hair, such as the skin on the head, neck, forehead and temple region is avoided insofar as possible.

In order to enable the most precise application possible, it is particularly advantage to package the agent as a stable foam. As a stable foam, the agent can completely envelop the hair, but does not have any flowing characteristics and remains in the exact location of the application.

For this reason, particular preference is given to a multi-component package unit (kit-of-parts) exemplified in that the first container (I) is an aerosol-type or non-aerosol-type foam-dispensing container.

For this reason, therefore, it is especially preferred that a multi-component package unit (kit-of-parts) is exemplified in that the first container (I) is an aerosol-type or non-aerosol-type foam-dispensing container.

In other words, it is especially preferred that a multi-component package unit (kit-of-parts) is exemplified in that the first container (I) is an aerosol pressure container.

The first container (I) can be an aerosol-type foam-dispensing container, i.e. an aerosol pressure container. Vessels made of metal (aluminum, tinplate, tin), protected or splinter-proof plastic or of glass that is coated on the outside with plastic are eligible as compressed gas containers, with compression strength, tensile strength, corrosion resistance, ease of filling, aesthetic aspects, portability, printability etc. being factors in their selection. Special inner coatings ensure corrosion resistance in relation to the preparation contained in the aerosol pressure container.

Particularly good effects as contemplated herein are attained if the internal pressure of the aerosol pressure container is at least about 1.8 bar, in particular at least about 2.5 bar.

In this case, container (I) comprises an aerosol dispensing device which has a valve to dispense the aerosol. In a preferred embodiment of the present disclosure, the valve has a valve head coated with a varnish or with a polymer plastic A, and a flexible element with resetting characteristics that resets the valve to the closing position (=resting position of the valve) after activation ceases. Corresponding multi-component units in which the aerosol dispensing device comprises a valve that has a valve cone and/or a flexible element with resetting characteristics that is/are coated with a varnish or a polymer plastic A are preferred as contemplated herein.

In a further preferred embodiment of the present disclosure, the valve has a flexible element with resetting characteristics and/or a valve head made of at least one plastic B, preferably an elastomer plastic. Here too, inventive cosmetic products in which the valve has a flexible element with resetting characteristics and/or a valve cone made of at least one plastic B are preferred, with preferred plastics B preferably being elastomer plastics. Particular preference is given to elastomer plastics selected from Buna, particularly Buna N, Buna N, Buna 421, Buna 1602 and Buna KA 6712, neoprene, butyl and chlorobutyl.

In a further preferred embodiment of the present disclosure, the flexible element can be formed with resetting characteristics as a coil spring or compression spring. In a further preferred embodiment of the present disclosure, the flexible element of the valve with resetting characteristics can be formed integrally with the valve cone and have flexible legs. This spring can be made of metal or plastic.

In a particularly preferred embodiment of the present disclosure, the valve cone and the flexible element are formed with resetting characteristics. The valve type Ariane M, available from Seaquist Perfect, in which the flexible element with resetting characteristics is formed integrally with the valve cone in the form of four elastic legs, is particularly preferred here.

All valves used as contemplated herein preferably have an inner-coated valve head, with the coating and the valve material being compatible with each other. If aluminum valves are used as contemplated herein, their valve heads can be coated on the inside with Micoflex varnish, for example. If tinsheet valves are used as contemplated herein, their valve heads can be coated on the inside with PET (polyethylene terephthalate), for example. The containers that are used can include, for instance, of tinsheet or aluminum, wherein aluminum containers are preferred as contemplated herein, the interior must also be painted or coated in consideration of the corrosiveness of the water used in oil emulsions as contemplated herein. An inner coating as contemplated herein is an epoxy phenolic varnish, as available under the designation Hoba 7407 P, for instance.

It is particularly preferred that the valve is a valve of the type Aptar ARM-4.00-1-0, 32-8, 70 Green—AR Housing—Valve-AHT-1,60-0,00-PA-Natural.

If container (I) is an aerosol-type foam-dispensing container, i.e. an aerosol pressure container, container (I) is also filled with at least one propellant gas and/or propellant. Suitable propellant gases or propellants can be selected from the group including propane, propene, n-butane, iso-butane, iso-butene, n-pentane, pentene, iso-pentane, iso-pentene, air, nitrogen, argon, $N_2O$ and/or $CO_2$.

Furthermore, particular preference is given to a multi-component package unit (kit-of-parts) exemplified in that container (I) contains at least one propellant.

Furthermore, particular preference is given to a multi-component package unit (kit-of-parts) exemplified in that container (I) contains at least one propellant from the group of propane, propene, n-butane, iso-butane, iso-butene, n-pentane, pentene, iso-pentane, iso-pentene, air, nitrogen, argon, $N_2O$ and/or $CO_2$.

It has been found to be preferable if the propellant gases are also contained in specific pressures in the dispenser. In a preferred embodiment, therefore, the dispensers as contemplated herein contain one or multiple additional propellant gases with a pressure of from about 3-about 12 bar, preferably from about 4 to about 10 bar and particularly from about 5 to about 8 bar—relative to the pressure of the propellant gases in container (I) in each case.

Furthermore, it is also especially preferred that a multi-component package unit (kit-of-parts) is exemplified in that the first container (I) is a non-aerosol-type foam-dispensing container.

A foam dispensing container of the non-aerosol type comprises at least one storage container (which contains the pre-treatment agent (V)) and an application device for dispensing the pre-treatment agent in the form of a foam. In the process, the storage container is designed, in particular, as a tubular or bottle-shaped container, whereas the application device closes this open container on one end. The actual preparation dispensing is initiated by employing manual pressure build-up by the user of the pre-treatment agent (V).

This manually actuated dispenser utilizes the users the action of force of the user in order to dispense a foamy preparation. The advantage of these designs is that an additional pressure source, such as a propellant, can be omitted, which is desirable with regard to costs and sustainability. Such foam dispensers actuated by manual exertion of force also ensure an appropriate foaming of the pre-treatment agent (V) in addition to the delivery of the pre-treatment agent (V) from the storage container to the dispensing opening. During the foaming or foam formation, the pre-treatment agent (V) is basically mixed with gaseous components, particularly air. To this end, a foaming device is provided specifically for this purpose.

In accordance with a first variant of a manually actuated dispenser, this foaming device is designed as a shaking dispenser having at least one storage container to accommodate the pre-treatment agent (V) and a corresponding dispensing device for the foaming dispensing of the pre-treatment agent (V). In the process, the dispensing device, which can be disconnected, is connected to the storage container. The actual foam formation takes place within the shaker dispenser by employing agitation of the pre-treatment agent (V) within the storage container. In this respect, the shaking dispenser forms the aforementioned foaming device in combination with the corresponding dispenser movement. After this type of foaming, the dispensing of the foamy pre-treatment agent (V) can take place by employing the dispensing device.

In a further advantageous dispenser variant, container (I) is designed as a squeeze foam dispenser. Such a squeeze foam dispenser has, in addition to the at least one storage container for accommodation of the pre-treatment agent (V), an application device within which the foaming and subsequent dispensing of the pre-treatment (V) take place. The actual delivery of the pre-treatment agent (V) from the storage container is caused by the exertion of force on the flexible storage container wall. In the process, the reversible deformation of the storage container wall ensures a pressure build-up inside the storage container, which consequently propels the pre-treatment agent (V) out of the storage container. For this purpose, it is necessary to design the storage container wall to be adequately flexible and/or reversible deformable. This is ensured with a targeted design of the storage container wall thickness for the application in combination with a suitable choice of material for the storage container wall. The storage container wall of a corresponding squeeze foam dispenser is preferably made of a polyolefin, such as polypropylene (PP), high density polyethylene (HDPE), medium density polyethylene (MDPE), low density polyethylene (LDPE), linear low-density polyethylene (LLDPE). Among these, polypropylene (PP) is preferred as suitable.

The application device of such a squeeze foam dispenser also comprises a foaming device for the foaming of the pre-treatment agent (V). The foaming device is capable of mixing an amount of preparation with an amount of gas in a suitable dispensing ratio in order to achieve the desired foam consistency of the pre-treatment agent (V). For this purpose, a drawn-in preparation flow is usually combined with a drawn-in gas flow within a mixing chamber of the foaming device and mixed there by fluidic turbulence. Particular preference is given to the use of air, which is drawn into the container directly from the storage container or the environment, as a gaseous component for foam formation.

The basic method of operation of such squeeze foam dispensers is also described in the documents WO 2007/086730 A2/A3 and EP 1237660 B1. An inventive squeeze foam dispenser can also be designed according to these patent documents. In particularly, the inventive squeeze foam dispenser in accordance with the disclosure of EP 1237660 B1 can be designed such that use of the squeeze foam dispenser is essentially possible in an upright position as well as upside-down.

Analogously, container (I) can also be designed as a pump foam dispenser having at least one storage container to accommodate the pre-treatment agent (V) and an application device, wherein the application device has a pump device for delivery of the pre-treatment agent (V) and the gaseous component, preferably air, and also has a foaming device. The method of operation and the design of such pump foam dispensers are also disclosed in the patent documents WO 2007/083206 A1 and WO 2007/091882 A1. In particular, the inventive pump foam dispenser can be designed in accordance with the disclosure of said documents.

Moreover, one or multiple porous insert elements can be used in the dispenser (corresponding to container (I)) in order to positively influence the achievable foam consistency within the foaming device. Such porous insert elements are, for example, have a sponge-like or mesh-like design and are positioned in a suitable position in the flow channel for the pre-treatment agent (V) within the foaming device, directly upstream of the dispenser opening. The porous insert element thereby enables the pre-treatment agent (V) to flow through and consequently ensures fluidic turbulence for a finer and more homogeneous foam consistence. The consistency of the foam can be directly influenced, depending on the specific design of the porous insert element. With use of a net-like insert element, it is advantageous to use the mesh-like insert element preferably with a hole density of from about 50 to about 220 mesh (mesh=number of holes per inch), more preferably from about 90 to about 200 mesh, particularly from about 125 to about 175 mesh. With use of multiple mesh-like insert elements, insert elements having different hole densities can also be used. In the process, the first mesh-like insert element positioned upstream preferably has a hole density of from about 50 to about 220 mesh (mesh=number of holes per inch), more preferably from about 90 to about 200 mesh, particularly from about 125 to about 175 mesh. The second mesh positioned downstream preferably has a hole density of from about 160 to about 280 mesh, more preferably from about 175 to about 245 and particularly from about 180 to about 220 mesh. Ultimately, the number of porous insert elements and their specific hole density and/or porosity characteristics are purposefully configured depending on the respective application case.

Furthermore, it is also especially preferred that a multi-component package unit (kit-of-parts) is exemplified in that the first container (I) is a squeeze foam dispenser or a pump foam dispenser.

Therefore, particular preference is also given to a method comprising the following steps in the specified sequence
A1) Application of a foamy pre-treatment agent (V) on the fibers,
A2) Allowing the pre-treatment agent (V) to take effect for a period of from about 30 seconds to about 45 minutes,
B1) Application of a coloring agent (F) on the fibers on which the pre-treatment agent (V) is still in place,
B2) Allowing the both agents (V) and (F) to take effect for a period of from about 30 seconds to about 45 minutes,
B3) Rinsing out of both agents (V) and (F),
Container (II)

After application of the pre-treatment agent (V), the inventive coloring agent (F) is applied on the keratinous fibers and/or hair. For this purpose, multi-component package unit as contemplated herein contains a second container which contains the coloring agent (F).

The coloring agent (F) can also be packaged in the form of a foam, and, therefore, tall statements made for container (I) also apply for container (II).

For this reason, particular preference is given to a multi-component package unit (kit-of-parts) exemplified in that the second container (II) is an aerosol-type or non-aerosol-type foam-dispensing container.

For this reason, therefore, it is especially preferred that a multi-component package unit (kit-of-parts) is exemplified in that the second container (II) is an aerosol-type or non-aerosol-type foam-dispensing container.

In other words, it is especially preferred that a multi-component package unit (kit-of-parts) is exemplified in that the second container (II) is an aerosol pressure container.

Furthermore, it is also especially preferred that a multi-component package unit (kit-of-parts) is exemplified in that the first container (I) is a non-aerosol-type foam-dispensing container.

Furthermore, it is also especially preferred that a multi-component package unit (kit-of-parts) is exemplified in that the second container (II) is a squeeze foam dispenser or a pump foam dispenser.

However, for cost purposes, it can also be advantageous to package the second container (II) as a standard tube or bottle and to package the coloring agent (F) as a gel or emulsion.

Applicators

The pre-treatment agent (V) and the coloring agent (F) can be applied on the hair to be treated by (gloved) hand or using a suitable applicator. Suitable applicators are, for example, brushes, applicettes or combs. A grommet or applicator device arranged on container (I) and/or (II) can also be used for applying the agents at the hair.

Pre-Treatment Agent (V)

The pre-treatment agent (V) is hydrous. The water content in the pre-treatment agent (V) can, for example, be in the range of from about 10.0 to about 95.0 wt. %, preferably from about 30.0 to about 95.0 wt. %, more preferably from about 50.0 to about 95.0 wt. % and particularly from about 70.0 to about 95.0 wt. %, relative to the total weight of the pre-treatment agent (V).

As contemplated herein, the hydrous pre-treatment agent (V) is adjusted to a pH value in the range of from about 0 to about 4.5. The pre-treatment agent is purposefully applied on the hair only such that the low pH value adjusted on or in the hair guarantees intense coloring of the hair. The pre-treatment agent (V) is not applied on the hair, in this manner, skin coloring from the applied coloring agent (F) is avoided during the later step B).

In general, the color uptake of acidic dyes on the hair is best with an acidic pH value. Although uptake of the acidic dyes on the hair fibers already takes place starting from a pH value of about 4.5, particularly intense coloring can be achieved if the pH value is adjusted to a value of less than or equal to about 4.0, preferably less than or equal to about 3.5, more preferably less than or equal to about 3.0 and most preferably less than or equal to about 2.0. For this reason, the pre-treatment agent (V) is preferably adjusted to these aforementioned pH value ranges.

Moreover, particular preference is thus given to a method as contemplated herein and a multi-component package unit as contemplated herein exemplified in that the pre-treatment agent (V) has a pH value of from about 0.2 to about 4.0, preferably from about 0.3 to about 3.5, more preferably from about 0.4 to about 3.0, even more preferably from about 0.5 to about 2.5 and particularly from about 0.5 to about 2.0.

Moreover, particular preference is thus given to a method as contemplated herein exemplified in that the pre-treatment agent (V) has a pH value of from about 0.2 to about 4.0, preferably from about 0.3 to about 3.5, more preferably from about 0.4 to about 3.0, even more preferably from about 0.5 to about 2.5 and particularly from about 0.5 to about 2.0.

Moreover, particular preference is thus given to a multi-component package unit as contemplated herein exemplified in that the pre-treatment agent (V) has a pH value of from about 0.2 to about 4.0, preferably from about 0.3 to about 3.5, more preferably from about 0.4 to about 3.0, even more preferably from about 0.5 to about 2.5 and particularly from about 0.5 to about 2.0.

One or multiple acids can be used to adjust the pH value. Suitable acids are inorganic acids, such as hydrochloric acid, sulfuric acid and/or phosphoric acid.

However, organic acids, such as acetic acid, lactic acid, citric acid, tartaricacid, malic acid, 1-hydroxy ethane-1,1-diphosphonic acid, 2,6-dipicolinic acid, benzoic acid maleic acid, succinic acid, oxalic acid, ascorbic acid, phytic acid and/or gluconic acid can also be used. In this connection, particular preference is given to low-odor acids such as lactic acid, citric acid, tartaric acid and/or malic acid and the inorganic acid is phosphoric acid.

Furthermore, particular preference is thus given to a method as contemplated herein and a multi-component package unit as contemplated herein exemplified in that the pre-treatment agent (V) contains an acid from the group including lactic acid, citric acid, tartaric acid, malic acid, 1-hydroxyethane-1,1-diphosphonic acid, 2,6-dipicolinic acid, benzoic acid, phosphoric acid, sulfuric acid, hydrochloric acid, maleic acid, succinic acid, oxalic acid, ascorbic acid, phytic acid and/or gluconic acid.

It has been found to be particularly beneficial when lactic acid, phosphoric acid and/or 1-hydroxy ethane-1,1 diphosphonic acid are used in the pre-treatment agent (V), because these acids do not tend to crystallize and, therefore, do not clog the path of the valve of an aerosol pressure container.

Furthermore, it is thus explicitly preferred that a method as contemplated herein and a multi-component package unit are exemplified in that the pre-treatment agent (V) contains at least one acid from the group including lactic acid, phosphoric acid and 1-hydroxy ethane-1,1 diphosphonic acid.

The pH value can be measured by employing a gas electrode, for example, which is usually in the form of a combination electrode. The pH values according to the present disclosure are pH values that were measured at a temperature of about 22° C.

In the context of the work leading up to this present disclosure, it has also been demonstrated that the use of a nonionic, film-forming and/or solidifying polymer in the pre-treatment agent (V) suppresses skin coloring in a particularly effective manner.

For this reason, it is particularly preferred that the pre-treatment agent (V) additionally contains at least one film-forming nonionic and/or solidifying nonionic polymer.

Polymers are macromolecules having a molecular weight of at least about 1000 g/mol, preferably at least about 2500 g/mol, more preferably at least about 5000 g/mol, which consist of the same, repeating organic units. Polymers are produced by polymerization of a monomer type or by polymerization of different, structurally different monomer types. If the polymer is produced by polymerization of one monomer type, it is referred to as a homopolymer. If structurally different monomer types are used in the polymerization process, the resultant polymer is referred to as a copolymer.

The maximum molecular weight of the polymer depends on the degree of polymerization (number of polymerized monomers) and is partly determined by the polymerization method. According to the present disclosure, the maximum molecular weight of the zwitterionic polymer (c) is preferably no more than about $10^7$ g/mol, more preferably no more than about $10^6$ g/mol and even more preferably no more than about $10^5$ g/mol.

As contemplated herein, a nonionic polymer is understood to mean a polymer which essentially has no structural units with permanent cationic or anionic groups in a protic solvent under standard conditions, which must be compensated for with counter-ions while maintaining electron neutrality. Cation groups include, for example, quaternated ammonia groups, but no protonated amines. Anionic groups include, for example, carboxylic and sulfonic acid groups.

The film-forming nonionic and/or solidifying nonionic polymers are preferably selected from at least one polymer of the group including homopolymers and nonionic copolymers of N-vinylpyrrolidone.

Suitable polyvinylpyrrolidones are, for example, commercial products such as Luviskol® K 90 or Luviskol® K 85 from the company BASF SE.

Agent containing, as a film-forming nonionic and/or solidifying nonionic polymer (c), at least one polymer from the group including
polyvinylpyrrolidone,
copolymers of N-vinylpyrrolidone and vinyl esters of carboxylic acids having from about 2 to about 18 carbon atoms, particularly N-vinylpyrrolidone and vinylacetate,
copolymers of N-vinylpyrrolidone and N-vinylimidazole and methacrylamide,
copolymers of N-vinylpyrrolidone and N-vinylimidazole and acrylamide,
copolymers of N-vinylpyrrolidone with N,N-Di($C_1$ to $C_4$)-alkylamino-($C_2$ bis $C_4$)-alkylacrylamide,
are particularly preferred as contemplated herein.

Suitable copolymerisates of vinylpyrrolidone and vinylacetate are available, for example under the trade names Luviskol® VA 37, Luviskol® VA 55, Luviskol® VA 64 and Luviskol® VA 73 from the company BASF SE.

Additional preferred agents as contemplated herein are exemplified in that they contain, as a nonionic film-forming and/or nonionic solidifying polymer (c), at least one copolymer (c1) which contains the at least one additional structural unit according to formula (I) and at least one structural unit according to formula (VII) and at least one structural unit according to formula (VIII)

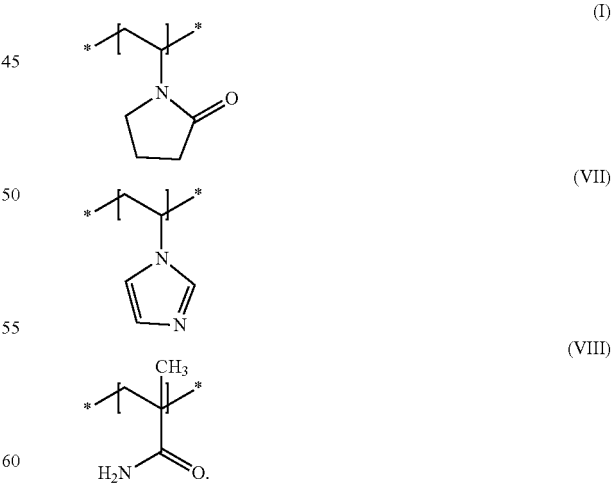

In this context, it is also particularly preferred if these copolymers contain, in addition to polymer units resulting from the integration of the indicated structural units according to formula (M1-a), (I), (VII) and (VIII) into the copolymer, a maximum of about 5 wt. %, preferably a maximum of about 1 wt. % of polymer units, which go back to the integration of other monomers. The copolymers (b3) preferably consists of structural units of formula (M1-a), (I), (VII) and (VIII) and can be described by the general formula (Poly4)

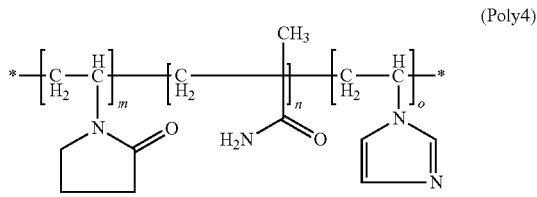

(Poly4)

wherein the indices m, n, o and p vary depending on the molar mass of the polymer and should not mean that they are block copolymers. Moreover, structural units of formulae (I), (VII) and (VIII) can be distributed statically in the molecule.

A particularly preferred polymer is selected from the polymers of the INCI name VP/Methacrylamide/Vinyl Imidazole Copolymer, which are available under the trade name Luviset Clear from the company BASF SE.

Furthermore, it has been found to be preferable to use agent containing at least one nonionic film-forming and/or nonionic solidifying polymer (c), comprising a structural unit of formula (I) and at least one structural unit of formula (III)

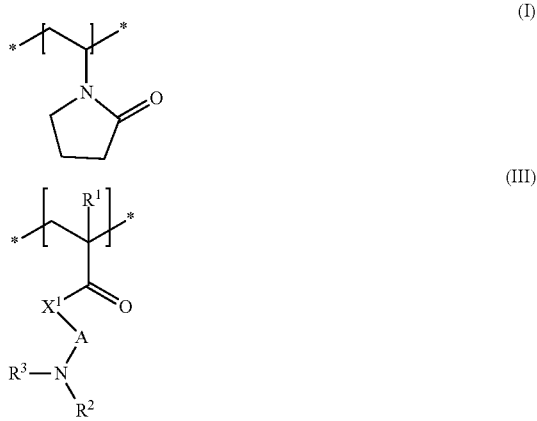

wherein
$R^1$ denotes a hydrogen atom or a methyl group,
$X^1$ denotes an oxygen atom or an NH group,
$A^1$ denotes an ethan-1,2-diyl, propan-1,3-diyl or butan-1,4-diyl group
$R^2$ and $R^3$, independently of each other, denote a ($C_1$ to $C_4$) alkyl group.

Furthermore, it is thus particularly preferred that a method as contemplated herein and a multi-component package unit as contemplated herein are exemplified in that the pre-treatment agent (V) contains at least one nonionic polymer from the group of homopolymers and copolymers of N-vinylpyrrolidone.

Furthermore, it is thus particularly preferred that a method as contemplated herein is exemplified in that the pre-treatment agent (V) contains at least one nonionic polymer from the group of homopolymers and copolymers of N-vinylpyrrolidone.

Furthermore, it is thus particularly preferred that a multi-component package unit are exemplified in that the pre-treatment agent (V) contains at least one nonionic polymer from the group of homopolymers and copolymers of N-vinylpyrrolidone.

Furthermore, it is thus explicitly preferred that a method as contemplated herein and a multi-component package unit as contemplated herein are exemplified in that the pre-treatment agent (V) contains at least one nonionic polymer from the group of
(i) polyvinylpyrrolidone,
(ii) copolymers of N-vinylpyrrolidone and vinyl esters of carboxylic acids having about 2 to about 18 carbon atoms, particularly N-vinylpyrrolidone and vinylacetate,
(iii) copolymers of N-vinylpyrrolidone and N-vinylimidazole and methacrylamide,
(iv) copolymers of N-vinylpyrrolidone and N-vinylimidazole and acrylamide,
(v) copolymers of N-vinylpyrrolidone with N,N-Di($C_1$ to $C_4$)-alkylamino-($C_2$ bis $C_4$)-alkylacrylamide.

The pre-treatment agent preferably contains the nonionic polymer or polymers in specific quantity ranges. It is preferred that the pre-treatment agent (V) contains—relative to the total weight of the pre-treatment agent (V)—one or multiple nonionic polymers in a total amount of from about 1.0 to about 12.0 wt. %, preferably from about 2.5 to about 10.0 wt. %, more preferably from about 3.5 to about 8.0 wt. % and particularly from about 4.5 to about 6.0 wt. %.

Furthermore, it is particularly preferred that a method as contemplated herein and a multi-component package unit as contemplated herein are exemplified in that the pre-treatment agent (V) contains one or multiple nonionic polymers in a total amount of from about 1.0 to about 12.0 wt. %, preferably from about 2.5 to about 10.0 wt. %, more preferably from about 3.5 to about 8.0 wt. % and particularly from about 4.5 to about 6.0 wt. %, relative to the total weight of the treatment agent (V).

Furthermore, it is particularly preferred that a method as contemplated herein is exemplified in that the pre-treatment agent (V) contains one or multiple nonionic polymers in a total amount of from about 1.0 to about 12.0 wt. %, preferably from about 2.5 to about 10.0 wt. %, more preferably from about 3.5 to about 8.0 wt. % and particularly from about 4.5 to about 6.0 wt. %, relative to the total weight of the pre-treatment agent (V).

Furthermore, it is particularly preferred that a multi-component package unit as contemplated herein is exemplified in that the pre-treatment agent (V) one or multiple nonionic polymers in a total amount of from about 1.0 to about 12.0 wt. %, preferably from about 2.5 to about 10.0 wt. %, more preferably from about 3.5 to about 8.0 wt. % and particularly from about 4.5 to about 6.0 wt. %, relative to the total weight of the pre-treatment agent (V).

As describe above, it has been found to be particularly preferable that the pre-treatment agent (V) is applied on the hair in foam form. This application in foam form can takes place, for example, by designing container (I) in the form of an aerosol-type or non-aerosol-type foam dispenser container.

In order to produce an especially stable foam, the pre-treatment agent (V) as contemplated herein preferably contains at least one surfactant.

The term surfactants is understood to mean surface-active substances that form adsorption layers on the top and boundary surfaces or in volume phases micell colloids or lyotropic mesophases. Anionic surfactants comprising a hydrophobic radical and a negatively charged hydrophilic head group differ from amphoteric surfactants, which have both a negative and a compensating positive charge, cationic surfactants, which, in addition to a hydrophobic radical, have a positively charged hydrophilic group, and nonionic surfactants, which do not have a charge and instead have strong dipole moments and are strongly hydrated in a hydrous solution.

The use of amphoteric and/or zwitterionic surfactants has been found to be particularly suitable.

Zwitterionic surfactants are surface active compounds, which have at least one quaternary ammonium group and at least one —COO$^{(-)}$— or —SO$_3^{(-)}$ group in the molecule. Particularly suitable zwitterionic surfactants are the so-called betaines such as the n-alkyl-n, n-dimethylammonium glycinates, for example coco-dimethylammonium glycinate, n-acylaminopropyl-n, n-dimethyl ammonium glycinates, for example coco-acylaminopropyldimethyl ammonium glycinate, and 2-alkyl-3-carboxymethyl-3-hydroxyethyl imidazolines each having from about 8 to about 18 carbon atoms in the alkyl or acyl group and coco-acylaminoethylhydroxyethyl carboxymethyl glycinate, as well as sultaines or sulfobetaines. A preferred zwitterionic surfactant is the fatty acid amide derivative known under the INCI trade name of Cocamidopropyl Betaine.

Ampholytic surfactants are understood to mean surfactant compounds which, apart from a $C_8$-$C_{24}$ alkyl or acyl group, contain at least one free amino group and at least one COOH or —SO$_3$H group in the molecule and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case from about 8 to about 24 carbon atoms in the alkyl group. Typical examples of amphoteric and/or zwitterionic surfactants are alkylbetaines, alkylamidobetaines, aminopropionates, aminoglycinates, imidazolinium betaines and sulfobetaines.

Particularly preferred ampholytic surfactants are N-cocosalkylaminopropionate, cocosacylaminoethylaminopropionate and $C_{12}$-$C_{18}$ acylsarcosin.

Particular preference is given to one or multiple surfactants from the group of amphoteric and zwitterionic surfactants in a total amount of from about 0.5 to about 10.5 wt. %, preferably from about 0.8 to about 8.5 wt. %, more preferably from about 1.1 to about 6.5 wt. % and particularly from about 1.4 to about 4.5 wt. %. All ampohteric and zwitterionic surfactants contained in the pre-treatment agent (V) are specified here as weight specifications in wt. % relative to the total weight of the pre-treatment agent (V).

Furthermore, it is thus particularly preferred that a method as contemplated herein and a multi-component package unit as contemplated herein are exemplified in that the pre-treatment agent (V) contains one or multiple amphoteric and/or zwitterionic surfactants in a total amount of from about 0.5 to about 10.5 wt. %, preferably from about 0.8 to about 8.5 wt. %, more preferably from about 1.1 to about 6.5 wt. %, and particularly from about 1.4 to about 4.5 wt. %, relative to the total weight of the treatment agent (V).

Furthermore, it is particularly preferred that a method as contemplated herein is exemplified in that the pre-treatment agent (V) contains one or multiple amphoteric and/or zwitterionic surfactants in a total amount of from about 0.5 to about 10.5 wt. %, preferably from about 0.8 to about 8.5 wt. %, more preferably from about 1.1 to about 6.5 wt. %, and particularly from about 1.4 to about 4.5 wt. %, relative to the total weight of the pre-treatment agent (V).

Furthermore, it is particularly preferred that a multi-component package unit as contemplated herein is exemplified in that the pre-treatment agent (V) contains one or multiple amphoteric and/or zwitterionic surfactants in a total amount of from about 0.5 to about 10.5 wt. %, preferably from about 0.8 to about 8.5 wt. %, more preferably from about 1.1 to about 6.5 wt. %, and particularly from about 1.4 to about 4.5 wt. %, relative to the total weight of the pre-treatment agent (V).

For the pre-treatment agent (V), all quantity specifications made in connection with the pre-treatment agent are relative to the total weight of the hydrous pre-treatment agent without propellant.

Coloring Agent (F)

The coloring agent (F) contains water and at least one partially-oxidizing acidic dye.

The water content in the coloring agent (F) can, for example, be in the range of from about 10.0 to about 95.0 wt. %, preferably from about 30.0 to about 95.0 wt. %, more preferably from about 50.0 to about 95.0 wt. % and particularly from about 70.0 to about 95.0 wt. %, relative to the total weight of the coloring agent (F).

Partially-oxidizing dyes can be categorized on the basis of their charge as cationic dyes (also referred to as basic dyes), nonionic dyes and anionic dyes (also referred to as acidic dyes). Acidic dyes are understood to mean partially-oxidizing dyes containing at least one carboxylic acid grouping (—COOH) and/or one sulfonic acid grouping (—SO$_3$H). Depending on the pH, the protonated forms (—COOH, —SO$_3$H) are present) of the carboxylic acid or sulfonic acid groupings with their deprotonated forms (—COO$^-$, —SO$_3^-$) in equilibrium. As the pH value decreases, the portion of protonated forms increases. If partially-oxidizing dyes in the form of their salts are used, the carboxylic acid groups and/or sulfonic acid groups are present in deprotonated form and are neutralized with appropriate stoichiometric equivalents on cations (such as Na-cation or K-cations) to maintain electron neutrality.

As suitable acid dyes, for example, one or more of the following compounds can be selected from the following group: Acid Yellow 1 (D&C Yellow 7, Citronin A, Ext. D&C Yellow No. 7, Japan Yellow 403, CI 10316, COLIPA no B001), Acid Yellow 3 (COLIPA n: C 54, D&C Yellow No 10, Quinoline Yellow, E104, Food Yellow 13), Acid Yellow 9 (CI 13015), Acid Yellow 17 (CI 18965), Acid Yellow 23 (COLIPA n° C. 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA no C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; no sodium salt; Brown No. 201; RESORCIN BROWN; ACID ORANGE 24; Japan Brown 201; D & C Brown No. 1), Acid Red 14 (C.I. 14720), Acid Red 18 (E124, Red 18; CI 16255), Acid Red 27 (E 123, CI 16185, C-Red 46, True Red D, FD&C Red Nr. 2, Food Red 9, Naphthol Red S), Acid Red 33 (Red 33, Fuchsia Red, D&C Red 33, CI 17200), Acid Red 35 (CI C.I.18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI 27290), Acid Red 87 (Eosin, CI 45380), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet no 2, C.I. 60730, COLIPA no C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido Blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black no 401, Naphthalene Black 10B, Amido Black 10B, CI 20 470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

Particular preference is given to a method of the first subject of the present disclosure exemplified in that the coloring agent (F) contains at least one partially-oxidizing acid from the group including Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 18, Acid Red 27, Acid Red 33, Acid Red 35, Acid Red 51, Acid Red 52, Acid Red 73, Acid Red 87, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 7, D&C Yellow 8, D&C Orange 4, D&C Green 5, D&C Orange 10, D&C Orange 11, D&C Red 21, D&C Red 27, D&C Red 33, D&C Violet 2 and/or D&C Brown 1.

Particular preference is given to a kit of the second subject of the present disclosure exemplified in that the coloring agent (F) contains at least one partially-oxidizing acid from the group including Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 18, Acid Red 27, Acid Red 33, Acid Red 35, Acid Red 51, Acid Red 52, Acid Red 73, Acid Red 87, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 7, D&C Yellow 8, D&C Orange 4, D&C Green 5, D&C Orange 10, D&C Orange 11, D&C Red 21, D&C Red 27, D&C Red 33, D&C Violet 2 and/or D&C Brown 1.

In summary, particular preference is given to a method as contemplated herein and a multi-component package unit exemplified in that the coloring agent (F) contains at least one partially-oxidizing acid from the group including Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 18, Acid Red 27, Acid Red 33, Acid Red 35, Acid Red 51, Acid Red 52, Acid Red 73, Acid Red 87, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 7, D&C Yellow 8, D&C Orange 4, D&C Green 5, D&C Orange 10, D&C Orange 11, D&C Red 21, D&C Red 27, D&C Red 33, D&C Violet 2 and/or D&C Brown 1.

Moreover, a particularly preferred method as contemplated herein and a particularly preferred kit as contemplated herein are thus exemplified in that the coloring agent (F) contains at least one of the following combination of partially-oxidizing acid dyes: Acid Yellow 1/Acid Orange 7; Acid Yellow 3/Acid Orange 7; Acid Yellow 9/Acid Orange 7; Acid Yellow 17/Acid Orange 7; Acid Yellow 23/Acid Orange 7; Acid Yellow 36/Acid Orange 7; Acid Yellow 121/Acid Orange 7; Acid Red 14/Acid Orange 7; Acid Red 18/Acid Orange 7; Acid Red 27/Acid Orange 7; Acid Red 33/Acid Orange 7; Acid Red 35/Acid Orange 7; Acid Red 51/Acid Orange 7; Acid Red 52/Acid Orange 7; Acid Red 73/Acid Orange 7; Acid Red 87/Acid Orange 7; Acid Red 95/Acid Orange 7; Acid Red 184/Acid Orange 7; Acid Red 195/Acid Orange 7; Acid Violet 43/Acid Orange 7; Acid Violet 49/Acid Orange 7 or Acid Violet 50/Acid Orange 7.

The acid dye and/or dyes can be preferably contained in the coloring agent (F) in a total amount of from about 0.01 to about 5.5 wt. %, more preferably from about 0.08 to about 4.7 wt. %, even more preferably from about 0.2 to about 3.4 wt. % and particularly from about 0.3 to about 1.8 wt. %. The total weight of the coloring agent (F) is used as a basis of calculation for the total amount of acid dyes specified in wt. %.

Furthermore, particular preference is thus given to a method of the first subject of the present disclosure or a kit of the second subject of the present disclosure exemplified in that the coloring agent (F) contains the partially-oxidizing acid dye or dyes in a total amount of from about 0.01 to about 5.5 wt. %, preferably from about 0.08 to 4.7 wt. %, more preferably from about 0.2 to about 3.4 wt. % and particularly from about 0.3 to about 1.8 wt. %, relative to the total weight of the coloring agent (F).

Furthermore, particular preference is thus given to a method of the first subject of the present disclosure exemplified in that the coloring agent (F) contains the partially-oxidizing acid dye or dyes in a total amount of from about 0.01 to about 5.5 wt. %, preferably from about 0.08 to about 4.7 wt. %, more preferably from about 0.2 to about 3.4 wt. % and particularly from about 0.3 to about 1.8 wt. %, relative to the total weight of the coloring agent (F).

Furthermore, particular preference is thus given to a kit of the second subject of the present disclosure exemplified in that the coloring agent (F) contains the partially-oxidizing acid dye or dyes in a total amount of from about 0.01 to about 5.5 wt. %, preferably from about 0.08 to about 4.7 wt. %, more preferably from about 0.2 to about 3.4 wt. % and particularly from about 0.3 to about 1.8 wt. %, relative to the total weight of the coloring agent (F).

An additional essential feature of the present disclosure is that the pH value of the coloring agent (F) is in the range from about 5.0 to about 9.5 and, therefore, in a neutral to alkaline range.

This neutral to alkaline pH value range is outside of the optimal pH value for coloring with acid dyes and, therefore, the coloring agent (F) itself does not produce any significantly coloring on the skin or the hair. Intense coloring only occurs where the hair was first treated with the pre-treatment agent (V).

In principle, the pH value of the coloring agent can be in the range of from about 5.0 to about 9.5, but particular preference is given to a slightly alkaline range. Therefore, it is particularly preferred that the coloring agent (F) has a pH value of from about 6.0 to about 9.0, preferably from about 6.5 to about 9.0, more preferably from about 7.0 to about 9.0, even more preferably from about 7.5 to about 9.0 and particularly from about 8.0 to about 9.0.

Therefore, particular preference is thus given to a method as contemplated herein and a multi-component package unit as contemplated herein exemplified in that the coloring agent (F) has a pH value of from about 6.0 to about 9.0, preferably from about 6.5 to about 9.0, more preferably from about 7.0 to about 9.0, even more preferably from about 7.5 to about 9.0 and particularly from about 8.0 to about 9.0.

Particular preference is given to a method as contemplated herein exemplified in that that the coloring agent (F) has a pH value of from about 6.0 to about 9.0, preferably from about 6.5 to about 9.0, more preferably from about 7.0 to about 9.0, even more preferably from about 7.5 to about 9.0 and particularly from about 8.0 to about 9.0.

Particular preference is given to multi-component package unit as contemplated herein exemplified in that the coloring agent (F) has a pH value of from about 6.0 to about 9.0, preferably from about 6.5 to about 9.0, more preferably from about 7.0 to about 9.0, even more preferably from about 7.5 to about 9.0 and particularly from about 8.0 to about 9.0.

The preferred and particularly preferred pH values in this context are advantageously adjusted with the addition of the necessary amounts of one or more alkalizing agents.

Inorganic compounds, preferably hydroxides or ammonias and organic bases, preferably amines, including, in particular alkanolamine can be used as alkalizing agents.

The alkali hydroxides that can be used as alkalizing agents as contemplated herein are preferably selected from the group including sodium hydroxide and potassium hydroxide.

The alkanolamines used as an alkalizing agent in the context of the present disclosure are preferably selected from primary amines with a $C_2$-$C_6$-alkyl base body having at least one hydroxyl group. Particularly preferred alkanolamines are selected from the group comprising 2-aminoethan-1-ol (monoethanolamine), 3-aminopropan-1-ol, 4-amino-butan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol. As contemplated herein, it is most preferable that alkanolamines are selected from the group of 2-aminoethan-1-ol, 2-amino-2-methylpropan-1-ol and 2-amino-2-methyl-propan-1,3-diol.

It is particularly preferred that the alkalizing agent is selected from at least one compound from the group including ammonia, 2-aminoethan-1-ol, 2-amino-2-methylpropane-1-ol, arginine, lysine, ornithine, histidine, potassium hydroxide, sodium hydroxide, magnesium hydroxide, calcium hydroxide, sodium metasilicate, potassium metasilicate, sodium carbonate, potassium carbonate, sodium bicarbonate and/or potassium bicarbonate.

Therefore, particular preference is thus given to a method as contemplated herein and a multi-component package unit as contemplated herein exemplified in that the coloring agent (F) contains at least one alkalizing agent from the group including ammonia, 2-aminoethan-1-ol, 2-amino-2-methylpropane-1-ol, arginine, lysine, ornithine, histidine, potassium hydroxide, sodium hydroxide, magnesium hydroxide, calcium hydroxide, sodium metasilicate, potassium metasilicate, sodium carbonate, potassium carbonate, sodium bicarbonate and/or potassium bicarbonate.

Moreover, it has been found to be particularly preferable that the coloring agent (F) contains one or more anionic polymers.

Therefore, it is particularly preferred that a method as contemplated herein and a multi-component package unit as contemplated herein are exemplified in that the coloring agent (F) contains at least one anionic polymer from the group of
(i) anionic polysaccharides,
(ii) polymers and copolymers of acrylic acid and/or methacrylic acid,
(iii) polymers and copolymers of 2-acrylamido-2-methyl-1-propanesulfonic acid,
(iv) polymers and copolymers of itaconic acid and
(v) polymers of maleic acid anhydride.

In another embodiment, the inventive agents can contain at least one (i) anionic polysaccharide as an anionic polymer. The group of (i) anionic polysaccharides includes xanthans, alginates, carboxyalkylcelluloses and hyaluronic acids.

Xanthan is an anionic polysaccharide which is composed of the structural components D-glucose, D-mannose, d-glucuronic acid, acetate and pyruvate and which is also known under the INCI name Xanthan Gum.

Salts of alginic acid are identified as alginates (INCI name Algin). Alginates are acidic carboxy groups containing polysacchardies including D-mannuronic acid and D-guluronic acid in varying ratios, which are linked with 1-4-glycosidic compounds. As contemplated herein, both alkali and earth alkali salts are aliginic acids. The use of aliginic acid, sodium alginate, potassium alginate, ammonium alginate and/or calcium alginate has been found to be particularly advantageous in the inventive agents. Carboxyalkyl celluloses are cellulose ethers, in which the hydrogen atoms of the hydroxyl groups of the cellulose are partially or completely substituted by carboxyalkyl groups. A preferred carboxyalkyl cellulose is carboxymethylcellulose, which can be used as an anionic polymer, preferably in the form of its sodium salt (sodium carboxymethylcellulose).

Basic building blocks of hyaluronic acid (INCI name hyaluronic acid, sodium hyaluronate) is an amino disaccharide constructed from D-glucuronic acid and N-acetylglucamine in 1-3-glycosidic bond, which is connected to the next unit β-1-4-glycosidically. In the context of the work leading to this present disclosure, sodium and potassium salts of hyaluronic acid have proven to be particularly suitable for producing intensely coloring formulations which are optimized with regard to their viscosity.

In this connection, it can be preferable that the coloring agent (F) contains one or more anionic polysaccharides exclusively as an anionic polymer.

In a further embodiment, the inventive agent (F) can contain at least (ii) one polymer of acrylic acid and/or methacrylic acid as an anionic polymer. The homopolymers and copolymers of acrylic acid and/or methacrylic acid are encompassed by the definition of a polymer. Homopolymers are, by definition, polymers arising from only one type. By contrast, copolymers are formed from multiple different monomers.

Homopolymers and copolymers of type (i) are exemplified in that they contain at least one structural unit of formula (P-I)

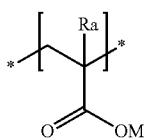

(P-I)

wherein

R1 denotes a hydrogen atom or a methyl group and
M denotes a hydrogen atom or sodium, potassium, ½ magnesium or ½ calcium.

A preferred homopolymer is a polyacrylic acid, such as those from 3V Sigma, which can be obtained under trade names of Synthalen K or Synthalen M, or from Lubrizol, which can be obtained under the trade names of Carbopol (for example, Carbopol 980, 981, 954, 2984 and 5984), each bearing the INCI name of Carbomer. The product sold by BASF under the trade name of Cosmedia SP (INCI Name: SODIUM POLYACRYLATE) can also be referred to as preferred acrylic acid homopolymer in this context.

The sodium acrylate/sodiumacryloyldimethyltaurate copolymers (INCI name: SODIUM ACRYLATE/SODIUM ACRYLOYLDIMETHYL TAURATE COPOLYMER, ISOHEXADECANE, POLYSORBATE 80) sold under the name Simulgel®EG have also been found to be particularly effective as contemplated herein as a compound with isohexadecane and polysorbate-80.

At least one copolymer of acrylic acid and/or methacrylic acid can also be used as an anionic polymer. A suitable polymer in this context is the polymer known under the INCI trade name of Acrylates/C10-30 Alkyl Acrylate Crosspolymer, which can be obtained under the trade name of Carbopol 1382 from Noveon. Another suitable polymer is the polymer known under the INCI trade name of Acrylates/Steareth-20 Methacrylate Crosspolymer, which is sold, for example, under the trade name of Aculyn® 88 by Rohm & Haas in the form of a from about 28 to about 30 wt. % dispersion. Other polymers according to the INCI nomenclature of Acrylates/Palmeth-25 Acrylate Copolymer or Acrylates/Palmeth-20 Acrylate Copolymer can also be used. Such polymers are, for example, available under the trade name Synthalen® W 2000 as a from about 30 to about 32 wt. % emulsion in water from the company 3 V Sigma.

Within this embodiment, it is also preferable to use a copolymer from at least one anionic acrylic acid and/or methacrylic acid monomer and at least one non-ionogenic monomer. Preferred non-ionogenic monomers in this context are acrylamide, methacrylamide, acrylic acid ester, methacrylic acid ester, vinylpyrrolidon, vinylether and vinylester.

Additional preferred anionic copolymers are copolymers from acrylic acid and/or methacrylic acid and the $C_1$-$C_6$-alkyl esters thereof, as sold under the INCI declaration Acrylates Copolymers. A preferred commercial product is, for example, Aculyn® 33 from Rohm & Haas. However, preferred copolymers from acrylic acid and/or methacrylic acid, the $C_1$-$C_6$ alkyl esters of acrylic acid and/or methacrylic acid, as well as the esters of ethylenically-unsaturated acids and an alkoxylated fatty alcohol. Suitable ethylenically unsaturated acids are, in particular, acrylic acid, methacrylic acid and itaconic acid; suitable alkoxylated fatty alcohols are, in particular, Steareth-20 or Ceteth-20. Such copolymers are sold by Rohm & Haas under the trade name Aculyn® 22 (INCI trade name: Acrylates/Steareth-20 Methacrylate Copolymer).

Further preferred anionic acrylic acid and/or methacrylic acid copolymers are acrylic acid acrylamide copolymers.

In a further preferred embodiment, the coloring agent (F) exclusively contains at least one homopolymer and/or copolymer of acrylic acid and/or methacrylic acid as an anionic polymer.

In a further preferred embodiment, a coloring agent (F) as contemplated herein contains at least (ii) one polymer of acrylic acid and/or methacrylic acid as an anionic copolymer, which is preferably selected from the substances known under the INCI names Carbomer (polyacrylic acid),
Sodium Polyacrylate,
Sodium Acrylate/Sodium Acryloyldimethyl Taurate Copolymer,
Acrylates/C10-30 Alkyl Acrylate Crosspolymer,
Acrylates/Steareth-20 Methacrylate Crosspolymer,
Acrylates/Palmeth-25 Acrylate Copolymer,
Acrylates/Palmeth-20 Acrylate Copolymer,
Acrylates Copolymers and/or
Acrylates/Steareth-20 Methacrylate Copolymer).

In a further embodiment, the coloring agent (F) as contemplated herein can contain (iii) a polymer of 2-acrylamido-2-methyl-1-propanesulfonic acid as an anionic polymer. The polymers of this category also comprise homo- and copolymers of 2-acrylamido-2-methyl-1-propanesulfonic in the context of the present disclosure.

Polymers of type (iii) are exemplified in that they contain at least one structural unit of formula (P-II) as a structural component,

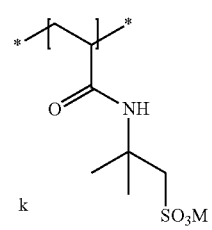

(II)

wherein
M denotes a hydrogen atom or sodium, potassium, ½ magnesium or ½ calcium.

Polymers of this type have anionic sulfonic acid groupings, which are introduced into the polymer by polymerization of the monomer 2-methyl-2-[(1-oxo-2-propenyl)amino]-1-propanesulfonic acid (AMPS). Anionic polymers which can contain 2-methyl-2[1-oxo-2-propenyl)amino]-1-propanesulfonic acid (AMPS as a sole monomer been found to be particularly effective, wherein the sulfonic acid group can be entirely or partly present as sodium-, potassium-, ammonium-, mono- or triethanol ammonium salt.

Homopolymers of 2-methyl-2[(1-oxo-2-propenyl)amino]-1-propanesulfonic acid have been found to be well-suited for use in the inventive agents. The compounds disclosed in the application EP 0815828 A1, which are polymers known under the name Cosmedia HSP 1160 as well as commercially available products sold under the name Rheothik® 11-80 have been found to be particularly suitable substances.

Polymers which are obtained by employing copolymerization of the 2-methyl-2-[1-oxo-2-propenyl)amino]-1-propanesulfonic acid building block with additional monomers are also comprised and preferred as contemplated herein.

A particularly preferred anionic copolymer of from about 70 to about 55 mol-% acryl amide and from about 30 to about 45 mol-% 2-acrylamido-2-methylpropane sulfonic acid, wherein the sulfonic acid group exists, either in whole or in part, as sodium, potassium, ammonium, mono or triethanol ammonium salt. This copolymer can also exist cross-linked, wherein polyolefinically unsaturated compounds, such as tetraallyloxythane, allylsucrose, allylpentaerythrite and methylen-bisacrylamide are preferably used as the cross-linking agents.

Additional preferred sulfonic acid polymers of this type are copolymers of 2-Methyl-2-[(1-oxo-2-propenyl)amino]-1-propane sulfonic acid (AMPS) and sodium acrylates, which can be obtained, for example, as a commercially available product Simulgel® EG (INCI name: Sodium Acrylates/Sodium Acryloyldimethyl Taurate Copolymer, Isohexadecane, Polysorbate 80) from the company Seppic.

Furthermore, it can be preferable that the coloring agent (F) exclusively contains at least one homo- and/or copolymer of 2-acrylamido-2-methyl-1-propane sulfonic acid as an anionic polymer (b).

In a further embodiment, the inventive agents can contain at least one (iv) polymer of itaconic acid and/or crotonic acid as an anionic polymer. The present disclosure comprises both homopolymers and copolymers of itaconic acid and/or crotonic acid. Polymers of this type are exemplified in that they contain at least on unit of formula (P-III) and/or formula (P-IV) as structural components,

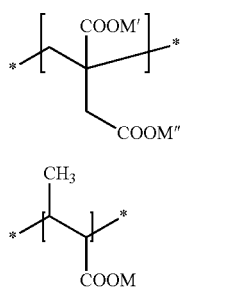

(P-III)

(P-IV)

wherein
M, M', M" denote, independently of each other, a hydrogen atom or sodium, potassium, ½ magnesium or ½ calcium.

A preferred copolymer belong in this class is, for example, the terpolymer that is commercially available under the trade name Vinnol E 15/45 M from the company Wacker Polymer Systems, which can be produced by employing the copolymerization of vinyl chloride, vinyl acetate and itaconic acid.

Moreover, it can be preferable that the coloring agent (F) exclusively contains (iv) one or more homopolymers and/or copolymers of itaconic acid and/or crotonic acid as an anionic polymer (b).

In another embodiment, the inventive agents can contain at least one (v) polymer of maleic acid anhydride as an anionic polymer (b). This groups includes homopolymers and copolymers containing at least one structural component of formula (P-V), which arises by employing the polymerization and hydrolysis of the maleic acid anhydride monomer building block,

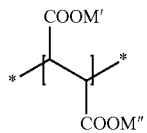

(P-V)

wherein
M', M" denote, independently of each other, a hydrogen atom or sodium, potassium, ½ magnesium or ½ calcium.

In this context, preferred anionic polymers are copolymers of maleic acid anhydride and methyl vinyl ether, particularly such with cross-linking. A maleic acid-methyl vinyl ether-copolymer cross-linked with 1,9-decadiene is commercially available under the trade name Stabileze® QM Finally, it can be preferable that the coloring agent (F) exclusively contains (v) one or more homopolymers and/or copolymers of maleic acid anhydride as an anionic polymer (b).

The pre-treatment agent (V) and-or coloring agent (F) can also contain additional active ingredients, adjuvants and additives in order to improve the coloring effect and set further desired properties of the agent.

Preferably, the (V) and (F) are provided as a liquid preparation and, if appropriate, a further surface-active substance is added to the agents, wherein such surface-active substances are referred to as surfactants or emulsifiers depending on the field of application: They are preferably selected from anionic, zwitterionic, amphoteric and nonionic surfactants and emulsifiers.

Suitable agents as contemplated herein are exemplified in that the agent additionally contains at least one anionic surfactant. Preferred anionic surfactants are fatty acids, alkyl sulfates, alkyl ether sulfates and ether carboxylic acids having from about 10 to about 20 C-atoms per alkyl group and up to about 16 glycol ether groups per molecule. The anionic surfactants are used in proportions from about 0.1 to about 45 wt. %, preferably from about 1 to about 30 wt. % and more preferably from about 1 to about 15 wt. %, relative on the total amount of the ready-to-use agent.

Suitable agents as contemplated herein are exemplified in that the agent additionally contains at least one amphoteric surfactant. Preferred zwitterionic surfactants are betaine, n-alkyl-n, n-dimethyl ammonium-glycinate, n-acyl-aminopropyl-n,n-dimethyl ammonium glycinate, and 2-alkyl-3-carboxymethyl-3-hydroxyethyl-imidazoline. A preferred zwitterionic surfactant is known by the INCI name cocamidopropyl betaine.

The coloring agent (F) can contain one or more amphoteric and/or zwitterionic surfactants. Suitable agents as contemplated herein are exemplified in that the agent additionally contains at least one amphoteric surfactant. Preferred amphoteric surfactants are n-alkylglycines, n-alkylpropionic acids, n-alkylaminobutyric acids, n-alkyliminodipropionic acids, n-hydroxyethyl-n-alkylamidopropylglycines, n-alkyltaurines, n-alkyl sarcosines, 2-alkylaminopropionic acids and alkylaminoacetic acids. Particularly preferred amphoteric surfactants are N-cocosalkylaminopropionate, cocosacylaminoethylaminopropionate and $C_{12}$-$C_{18}$ acylsarcosin.

It has also proved advantageous for agents to contain other, non-ionogenic surfactants. Preferred non-ionic surfactants are alkyl polyglycosides as well as alkylene oxide binding agents to fatty alcohols and fatty acids with from about 2 to about 30 moles of ethylene oxide per mole of fatty alcohol or fatty acid. Preparations with outstanding properties are also obtained if they contain fatty acid esters of ethoxylated glycerol as nonionic surfactants.

The nonionic, zwitterionic or amphoteric surfactants can be used in volumes from about 0.1 to about 45 wt. %, preferably from about 1 to about 30 wt. % and especially preferably from about 1 to about 15 wt. %—relative to the total amount of ready-to-use agents.

It has also been found to be beneficial that the agents contain at least one thickening agent. There are essentially no limitations with respect to these thickening agents. Organic and purely inorganic thickening agents can be used. Suitable thickening agents are anionic, synthetic polymers, cationic, synthetic polymers, naturally occurring thickening agents, such as nonionic guargium, scleroglucan, or xanthangium, gum arabic, ghatti gum, karaya gum, tragacanth gum, carrageenan gum, agar-agar, locust bean flour, pectins, alginates, starch fractions and derivatives such as amylose, amylopectin and dextrins, and cellulose derivatives, such as, for example, methyl cellulose, carboxyalkyl celluloses and hydroxyalkyl celluloses, non-ionic, fully synthetic polymers, such as polyvinyl alcohol or polyvinylpyrrolidinone; and inorganic thickening agents, in particular phyllosilicates such as, for example, bentonite, particularly smectites such as montmorillonite or hectorite.

The agents (V) and/or (F) can also contain anionic polymeric thickening agents. Suitable compounds are, for example, selected from the cross-linked or non-cross-linked copolymers containing at least two different monomers from the group of acrylic acid, methacrylic acid, $C_1$-$C_6$ alkyl esters of acrylic acid and/or $C_1$-$C_6$ alkyl esters of methacrylic acid. Particular preferred anionic copolymers are copolymers from acrylic acid, methacrylic acid or the $C_1$-$C_6$-alkyl esters thereof, as sold under the INCI declaration Acrylates Copolymers. Particular preference is given to the combination of methacrylic acid an ethylacrylate, as well as cross-linked multifunctional monomers, if applicable. An example of a preferred commercially available product for this purpose is Aculyn® 33 or 33A, from the company Rohm & Haas.

The agents (V) and/or (F) can also contain cationic polymers.

With respect to minimizing hair damage, it has been found to be particularly advantageous that the agents (V) and/or (F) contain one or multiple polymers from the group consisting of Polyquaternium-1, Polyquaternium-2, Polyquaternium-3, Polyquaternium-4, Polyquaternium-5, Polyquaternium-6, Polyquaternium-7, Polyquaternium-8, Polyquaternium-9, Polyquaternium-10, Polyquaternium-11, Polyquaternium-14, Polyquaternium-16, Polyquaternium-17, Polyquaternium-18, Polyquaternium-22, Polyquaternium-24, Polyquaternium-27, Polyquaternium-28, Polyquaternium-32, Polyquaternium-33, Polyquaternium-37, Polyquaternium-39, Polyquaternium-44, Polyquaternium-46, Polyquaternium-53, Polyquaternium-55, Polyquarternium-64, Polyquaternium-67, Polyquaternium-68, Polyquaternium-69 and/or Polyquaternium-86.

Methods and kits preferred as contemplated herein, therefore, are exemplified in that the agents (V) and/or (F) also contain one or multiple cationic surfactants. As contemplated herein all common cationic surfactants known to the person skilled in the art can be used as cationic surfactants.

The surfactants (T) are used in a total amount of the surfactants in amounts of from about 0.05-about 45 wt. %, preferably from about 0.1-about 30 wt. %, and particularly from about 0.5-about 25 wt. %, relative to the total amount of the agents used as contemplated herein.

The cationic surfactants can be used in amounts from about 0.1 to about 45 wt. %, preferably from about 1 to about 30 wt. % and especially preferably from about 1 to about 15 wt. %—relative to the total amount of the respective agent (V) and/or (F) in each case.

Moreover, the inventive agents can contain additional active ingredients, adjuvants and additives, such as fatty alcohols, nonionic polymers such as vinylpyrrolidinon/vinylacrylat-copolymers, polyvinylpyrrolidinon, vinylpyrrolidinon/vinylacetat-copolymers, polyethylenglycols and polysiloxanes; additional silicones such as volatile or non-volatile, straight-chained, branched or cyclical, cross-linked or non-cross-linked polyalkylsiloxanes (such as dimethicones or cyclomethicones), polyarylsiloxanes and/or polyalkylarylsiloxanes, more particularly polysiloxanes with organofunctional groups such as subtituted or unsubstituted amines (amodimethicones), carboxyl-, alkoxy- and/or hydroxyl groups (dimethiconcopolyols), lineare polysiloxan (A)-polyoxyalkylen(B)-block copolymers, grafted silicon polymers; cationic polymers such as quaternized cellulose ether, polysiloxanes with quaternary groups, dimethyldiallylammoniumchlorid-polymers, acrylamid-dimethyldiallylammonium chloride copolymers, with diethylsulfate quaternated dimethylamino-ethylmethacrylat-vinylpyrrolidinon-copolymers, vinylpyrrolidinon-imidazoliniummethochlorid-copolymers and quaternated polyvinylalcohol; zwitterionic and amphoteric polymers; anionic polymers such as polyacrylic acids or cross-linked polyacryl acids; structurants, such as glucose, malic acid and lactic acid, hair-conditioning compounds such as phospholipides, for example lecithin and kephaline; perfume oils, dimethylisosorbid and cyclodextrine; fiber structure-improving agents, more particularly mono-, di- and oligosaccharides, such as glucose, galactose, fructose, fruit sugar and lactose; dyes for coloring the preparations; anti-dandruff active ingredients such as piroctone olamine, zinc omadine and climbazol; amino acids and oligopeptides; protein hydrolysates on an animal and/or plant basis, as well as in the form of their fatty acid condensation products or, where applicable, anionically or cationically modified derivatives; plant oils; light stabilizers and UV blockers; active ingredients such as panthenol, pantothenic acid, pantolacton, allantoin, pyrrolidinoncarbonic acids and the salts thereof, as well as bisabolol; polyphenols, more particularly hydroxy cinnamic acids, 6,7-dihydroxycumarines, hydroxybenzoic acids, catechins, tannins, leukoanthocyanidine, anthocyanidine, flavanons, flavons and flavonols; ceramides or pseudoceramides; vitamins, provitamins and vitamin precursors; plant extracts; fats and waxes such as fatty alcohols, beeswax, montan wax and paraffins; source and penetration substances such as glycerin, propylene glycolmonoethylether, carbonate, hydrogen carbonate, guanidine, urea, as well as primary, secondary and tertiary phosphates; opacifiers such as latex, styrene/PVP and styrene/acrylamide copolymers; pearl shine concentrates such as ethylenglycolmono- and -distearate as well as PEG-3-distearate; pigments as well as propellants such as propane-butane-mixtures, $N_2O$, dimethylether, $CO_2$ and air.

The person skilled in the art will select these other substances in accordance with the desired properties of the agent. With regard to further optional components and the amounts of these components used, reference is expressly made to the relevant handbooks known to the person skilled in the art. In the agents as contemplated herein, the additional active ingredients and excipients are preferably used in quantities of from about 0.0001 to about 25 wt. %, particularly from about 0.0005 to about 15 wt. %, relative to the total weight of the respective agent.

EXAMPLES

The following formulations have been produced—unless otherwise stated, all values refer to percentage by weight.

1. Pre-Treatment Agent (V)

| Pre-treatment agent (V) (wt. %) | (V1) |
|---|---|
| Glycerol | 0.3 |
| Cocoamidopropylbetaine (40% hydrous solution) | 2.0 |
| Copolymer of polyvinylpyrrolidone/vinyl acetate (60 mol % polyvinylpyrrolidone, 40 mol % vinyl acetate) | 5.0 |
| Castor oil, hydrogenated, 40 EO | 0.5 |
| Lactic acid (80% hydrous solution) | ad pH 0.5 |
| Water (dist.) | ad 100 |

An aerosol pressure container was filled with 90 g of pre-treatment agent and 10 g of propellant (propane/butane).

2. Coloring Agent (F)

| | Coloring agent (F) | | |
|---|---|---|---|
| | (F1) | (F2) | (F3) |
| Ceteareth-12 | 2.9 | 2.9 | 2.9 |
| Phenoxyethanol | 0.8 | 0.8 | 0.8 |
| Ext. D&C Violet 2 (Acid Violet 43, CI 60730, CAS no. 4430-18-6) | 0.2 | 0.2 | 0.2 |
| Xanthan | 2.0 | 2.0 | 2.0 |
| Benzyl alcohol | 4.0 | 4.0 | 4.0 |
| KOH | ad pH 2.7 | ad pH 5.3 | ad pH 8.6 |
| Water | ad 100 | ad 100 | ad 100 |

3. Hair Studio Tests

Comparison: The coloring agent (F) was applied to the hair of a test subject and allowed to take effect for 30 minutes. Then the hair was rinsed out with warm water and dried.

Method as contemplated herein: The pre-treatment agent (V) was foamed from the aerosol pressure container onto a comb and incorporated into the hair of a test subject with the comb. The foam was allowed to take effect for 10 minutes. Then one of the coloring agents (F) was applied to the hair in which the pre-treatment agent (V) was still incorporated. The coloring agent (F) was allowed to take effect for 30 minutes. Then the hair was rinsed out with warm water and dried. After the hair was dried, the color intensity of the dyed hair and the skin coloring were evaluated visually.

| | Comparison 1 | Comparison 2 | Comparison 3 | Embodiment 1 |
|---|---|---|---|---|
| A1) Pre-treatment agent (V) application | — | — | — | (V1) pH 0.5 |
| B1) Coloring agent (F) application | (F1) pH 2.7 | (F2) pH 5.3 | (F3) pH 8.6 | (F3) pH 8.6 |
| Color intensity | +++ | + | − | +++ |
| Skin coloring | +++ | + | − | − |

+++ = very high
++ = high + = moderate
− = low

4. Determination of Color Intensity (Hair Strands)

Hair strands (Kerling 6-0) were measured with a colorimeter from Datacolor, type Spectraflash 450.

Comparison: The coloring agent (F) was applied to hair strands and allowed to take effect for 30 minutes. Then the hair was rinsed out with warm water and dried.

Method as contemplated herein: The pre-treatment agent (V) was foamed from the aerosol pressure container onto a comb and incorporated into the hair strands with the comb. The foam was allowed to take effect for 10 minutes. Then one of the coloring agents (F) was applied to the hair in which the pre-treatment agent (V) was still incorporated. The coloring agent (F) was allowed to take effect for 30 minutes. Then the hair was rinsed out with warm water and dried.

After drying, the hair strands were measured again by colorimetry.

The ΔE value used for evaluation of the color intensity arises from the L*a*b* color measurement values as follows:

$$\Delta E = [(L_i - L_0)^2 + (a_i - a_0)^2 + (b_i - b_0)^2]^{1/2}$$

$L_0$, $a_0$ and $b_0$: Color measurement values before coloring
$L_i$, $a_i$ and $b_i$: Color measurement values after coloring The ΔE value indicates the color difference between the undyed and dyed hair. The greater the ΔE value is, the greater the color difference is between the undyed and dyed hair and thus the more intense the coloring on the hair.

| Hair strand color intensity | Comparison 1 | Comparison 2 | Comparison 3 | Embodiment 1 |
|---|---|---|---|---|
| A1) Pre-treatment agent (V) application | — | — | — | (V1) pH 0.5 |
| B1) Coloring agent (F) application | (F1) pH 2.7 | (F2) pH 5.3 | (F3) pH 8.6 | (F3) pH 8.6 |
| ΔE value (hair) | 49.2 | 18.1 | 13.5 | 47.9 |
| Color intensity | +++ | + | − | +++ |

5. Determination of Skin Coloring (Underarm)

Areas of skin on the under arm were measured by colorimetry using a portable colorimeter from the company X-Right, type eXact. Then the areas were treated with the method describe above. After rinsing out the coloring agent, the treated areas were measured again using colorimetry.

The ΔE value used for evaluation of the color intensity arises from the L*a*b* color measurement values as follows:

$$\Delta E = [(L_i - L_0)^2 + (a_i - a_0)^2 + (b_i - b_0)^2]^{1/2}$$

$L_0$, $a_0$ and $b_0$: Color measurement values before coloring
$L_i$, $a_i$ and $b_i$: Color measurement values after coloring The ΔE value indicates the color difference between the treated and untreated skin. The greater the ΔE value is, the greater the color difference is between the undyed and dyed skin and thus the stronger the skin coloring.

| Skin color intensity | Comparison 1 | Comparison 2 | Comparison 3 |
|---|---|---|---|
| A1) Pre-treatment agent (V) application | — | — | — |
| B1) Coloring agent (F) application | (F1) pH 2.7 | (F2) pH 5.3 | (F3) pH 8.6 |
| ΔE value (skin) | 35.7 | 14.2 | 12.3 |
| Skin coloring | +++ | − | − |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. Method for coloring of keratinous fibers comprising the following steps in the specified sequence:
A) treating the fibers with a hydrous pre-treatment agent (V),
B) treating the fibers with a hydrous coloring agent (F), wherein
the hydrous pre-treatment agent (V) has a pH value of from about 0 to about 4.5, wherein the hydrous pre-treatment agent (V) comprises a copolymer of polyvinylpyrrolidone/vinyl acetate and betaine and the hydrous coloring agent (F) has at least one partially-oxidizing acid dye, at least one anionic polymer, and a pH value of from about 5.0 to about 9.5.

2. Method according to claim 1 comprising the following steps in the specified sequence:
A1) applying the hydrous pre-treatment agent (V) on the fibers,
A2) allowing the hydrous pre-treatment agent (V) to take effect for a period of from about 30 seconds to about 45 minutes,
B1) applying the hydrous coloring agent (F) on the fibers on which the hydrous pre-treatment agent (V) is still in place,
B2) allowing both the hydrous pre-treatment agent (V) and the hydrous coloring agent (F) to take effect for a period of from about 30 seconds to about 45 minutes, and
B3) rinsing out both the pre-treatment hydrous agent (V) and the hydrous coloring agent (F).

3. Multi-component package unit for coloring of keratinous fibers comprising, separately packaged
(I) a first container (I) comprising a hydrous pre-treatment agent (V) wherein the hydrous pre-treatment agent (V) comprises a copolymer of polyvinylpyrrolidone/vinyl acetate and betaine, and
(II) a second container (II) comprising a hydrous coloring agent (F),
wherein the hydrous pre-treatment agent (V) has a pH value of from about 0 to about 4.5, and the hydrous coloring agent (F) has at least one partially-oxidizing acid dye, at least one anionic polymer, and a pH value of from about 5.0 to about 9.5.

4. Multi-component package unit according to claim 3, wherein the first container (I) is a foam dispenser container.

5. Method according to claim 1, wherein the hydrous pre-treatment agent (V) has a pH value of from about 0.2 to about 4.0.

6. Method according to claim 1, wherein the hydrous pre-treatment agent (V) comprises an acid selected from the group of lactic acid, citric acid, tartaric acid, malic acid, 1-hydroxyethane-1,1-diphosphonic acid, 2,6-dipicolinic acid, benzoic acid, phosphoric acid, sulfuric acid, hydrochloric acid, maleic acid, succinic acid, oxalic acid, ascorbic acid, phytic acid, gluconic acid, or combinations thereof.

7. Method according to claim 1, wherein the hydrous pre-treatment agent (V) comprises a homopolymer of N-vinylpyrrolidone.

8. Method according to claim 1, wherein the hydrous pre-treatment agent (V) comprises one or multiple nonionic polymers in a total amount of from about 1.0 to about 12.0 wt. %.

9. Method according to claim 1, wherein the hydrous pre-treatment agent (V) comprises one or multiple amphoteric and/or zwitterionic surfactants in a total amount of from about 0.5 to about 10.5 wt. %.

10. Method according to claim 1, wherein the hydrous coloring agent (F) comprises at least one partially-oxidizing acid selected from the group of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 18, Acid Red 27, Acid Red 33, Acid Red 35, Acid Red 51, Acid Red 52, Acid Red 73, Acid Red 87, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 7, D&C Yellow 8, D&C Orange 4, D&C Green 5, D&C Orange 10, D&C Orange 11, D&C Red 21, D&C Red 27, D&C Red 33, D&C Violet 2, D&C Brown 1, or combinations thereof.

11. Method according to claim 1, wherein the hydrous coloring agent (F) has a pH value of from about 6.0 to about 9.0.

12. Method according to claim 1, wherein the hydrous coloring agent (F) comprises at least one alkalizing agent selected from the group of ammonia, 2-aminoethan-1-ol, 2-amino-2-methylpropane-1-ol, arginine, lysine, ornithine, histidine, potassium hydroxide, sodium hydroxide, magnesium hydroxide, calcium hydroxide, sodium metasilicate, potassium metasilicate, sodium carbonate, potassium carbonate, sodium bicarbonate, potassium bicarbonate, or combinations thereof.

13. Method according to claim 1, wherein the hydrous coloring agent (F) comprises at least one anionic polymer selected from the group of
(i) anionic polysaccharides,
(ii) polymers and copolymers of acrylic acid and/or methacrylic acid,
(iii) polymers and copolymers of 2-acrylamido-2-methyl-1-propanesulfonic acid,
(iv) polymers and copolymers of itaconic acid,
(v) polymers of maleic acid anhydride, or combinations thereof.

14. Method according to claim 1, wherein the hydrous pre-treatment agent (V) has a pH value of from about 0.3 to about 3.5.

15. Method according to claim 1, wherein the hydrous pre-treatment agent V comprises one or multiple nonionic polymers in a total amount of from about 2.5 to about 10.0 wt. %.

16. Method according to claim 1, wherein the hydrous pre-treatment agent (V) comprises one or multiple amphoteric and/or zwitterionic surfactants in a total amount of from about 0.8 to about 8.5 wt. % relative to the total weight of the pre-treatment agent (V).

17. Method according to claim 1 wherein the hydrous coloring agent (F) has a pH value of from about 6.5 to about 9.0.

18. Method according to claim 1, wherein the hydrous coloring agent (F) is free from oxidation dye precursors.

19. Multi-component package unit for coloring of keratinous fibers comprising, separately packaged
(I) a first container (I) comprising a hydrous pre-treatment agent (V), wherein the hydrous pre-treatment agent (V) has a pH value of from about 0 to about 4.5 and comprises an acid, one or multiple nonionic polymers in a total amount of from about 1.0 to about 12.0 wt. %, and one or multiple amphoteric and/or zwitterionic surfactants in a total amount of from about 0.5 to about 10.5 wt. %, wherein the hydrous pre-treatment agent (V) comprises a copolymer of polyvinylpyrrolidone/vinyl acetate and betaine; and
(II) a second container (II) comprising a hydrous coloring agent (F), wherein the hydrous coloring agent (F) has a pH value of from about 5.0 to about 9.5 and comprises at least one partially-oxidizing acid dye, at least one anionic polymer, at least one alkalizing agent.

20. Multi-component package unit according to claim 19, wherein:
the hydrous pre-treatment agent (V) has a pH of from about 0.3 to about 3.5 and comprises the copolymer of polyvinylpyrrolidone/vinyl acetate in a total amount of from about 3.5 to about 8.0 wt. %, and cocoamidopropylbetaine in a total amount of from about 1.4 to about 4.5 wt. %; and
the hydrous coloring agent (F) has a pH of from about 6.5 to about 9.0 and comprises the at least one partially-oxidizing acid dye in a total amount of from about 0.2 to about 3.4 wt. %, xanthan as the at least one anionic polymer, wherein the hydrous coloring agent (F) is free from oxidation dye precursors.

* * * * *